(12) United States Patent
LaBorde et al.

(10) Patent No.: US 7,323,139 B2
(45) Date of Patent: Jan. 29, 2008

(54) ACCESSIBLE ASSAY AND METHOD OF USE

(75) Inventors: Ronald T. LaBorde, San Diego, CA (US); Randall N. Taff, San Diego, CA (US); David M. Pratt, Carlsbad, CA (US)

(73) Assignee: Quantum Design, Inc., San Deigo, CA (US)

( * ) Notice: Subject to any disclaimer, the term of this patent is extended or adjusted under 35 U.S.C. 154(b) by 625 days.

(21) Appl. No.: 10/422,336

(22) Filed: Apr. 24, 2003

(65) Prior Publication Data

US 2004/0214347 A1 Oct. 28, 2004

Related U.S. Application Data

(60) Provisional application No. 60/398,758, filed on Jul. 26, 2002.

(51) Int. Cl.
| | |
|---|---|
| G01N 21/27 | (2006.01) |
| G01N 21/64 | (2006.01) |
| G01N 27/72 | (2006.01) |
| G01N 27/90 | (2006.01) |
| G01N 31/22 | (2006.01) |
| G01N 33/553 | (2006.01) |

(52) U.S. Cl. ............... 422/58; 422/56; 422/57; 436/149; 436/177; 436/526

(58) Field of Classification Search ............ 422/56–58; 436/58, 149, 177, 525–526, 824
See application file for complete search history.

(56) References Cited

U.S. PATENT DOCUMENTS

| | | | | |
|---|---|---|---|---|
| 3,884,641 | A | * | 5/1975 | Kraffczyk et al. ........ 435/287.9 |
| 4,857,453 | A | * | 8/1989 | Ullman et al. ............. 435/7.92 |
| 4,999,285 | A | | 3/1991 | Stiso |
| 5,006,474 | A | * | 4/1991 | Horstman et al. .......... 436/524 |
| 5,066,465 | A | * | 11/1991 | Kano et al. ................... 422/58 |
| 5,087,556 | A | | 2/1992 | Ertinghausen |
| 5,173,261 | A | * | 12/1992 | Krause et al. ................ 422/58 |
| 5,399,316 | A | * | 3/1995 | Yamada ....................... 422/58 |
| 5,416,000 | A | | 5/1995 | Allen et al. |
| 5,622,871 | A | * | 4/1997 | May et al. ................... 436/514 |
| 5,728,587 | A | | 3/1998 | Kang et al. |
| 5,759,492 | A | * | 6/1998 | Reale .......................... 422/58 |
| 5,962,336 | A | | 10/1999 | Sun |
| 5,997,817 | A | * | 12/1999 | Crismore et al. ........ 204/403.1 |
| 6,248,598 | B1 | | 6/2001 | Bogema |
| 6,372,516 | B1 | | 4/2002 | Sun |
| 6,607,922 | B2 | * | 8/2003 | LaBorde ..................... 436/514 |
| 6,766,817 | B2 | | 7/2004 | da Silva |

* cited by examiner

*Primary Examiner*—Arlen Soderquist
(74) *Attorney, Agent, or Firm*—The Maxham Firm (57) ABSTRACT

An assay test strip and cassette. The test strip is positioned in a housing shaped and configured to allow a detector to access the test strip from the side, rather than from the lengthwise axis of the test strip. The housing may contain one or more test strips which may also be disposed on one or more surfaces of the housing. Preferably, the housing is generally C-shaped with the test strip spanning the space between the two arms of the C-shape. The housing is sealed to protect both the operator and instrument from possible contamination. The test strip is preferably embedded with paramagnetic particles and process chemistry specific for a particular application. Quantitative analysis may be accomplished using a magnetic reader device. In additional embodiments, detection is accomplished by visual means.

26 Claims, 4 Drawing Sheets

ACCESSIBLE ASSAY AND METHOD OF USE

CROSS-REFERENCE TO RELATED APPLICATION

This application claims the benefit of U.S. Provisional Application No. 60/398,758, filed 26 Jul. 2002.

BACKGROUND OF INVENTION

1. Field of Invention

The present invention relates generally to assays, and more specifically to a lateral flow assay device with improved detection access.

2. Discussion of Related Art

Various chromatographic immunoassay techniques have been available for many years. Tests that can be performed with such chromatographic systems are, among others, immunoassays, which depend on the specific interaction between an antigen or hapten and a corresponding antibody. Immunoassays have been used as a means of testing for the presence or amount, or both, of clinically important molecules for some time. Immune-based latex agglutination tests for detecting a factor associated with rheumatoid arthritis were used as early as 1956 (Singer et al., *Am. J. Med.* 22:888-892 (1956)).

Among the many analytical systems used for detection of analytes, particularly analytes of biological interest, are chromatographic assay systems. Among the analytes frequently assayed with such systems are: (1) hormones, such as human chorionic gonadotropin (hCG), which is frequently assayed as a marker of human pregnancy; (2) antigens, particularly antigens specific to bacterial, viral, and protozoan pathogens, such as streptococcus, hepatitis virus, and giardia; (3) antibodies, particularly antibodies induced as a result of infection with pathogens, such as antibodies to the bacterium HELICOBACTER pylori and to Human Immunodeficiency Virus (HIV); (4) other proteins, such as hemoglobin, frequently assayed in determinations of fecal occult blood, an early indicator of gastrointestinal disorders such as colon cancer; (5) enzymes, such as aspartate aminotransferase, lactate dehydrogenase, alkaline phosphatase, and glutamate dehydrogenase, frequently assayed as indicators of physiological function and tissue damage; (6) drugs, both therapeutic drugs, such as antibiotics, tranquilizers and anticonvulsants, and illegal drugs of abuse, such as cocaine, heroin and marijuana; (7) vitamins; and (8) nucleic acid material.

Such chromatographic systems are frequently used by physicians and medical technicians for rapid in-office diagnosis, commonly referred to as "point of care" (POC) devices, and therapeutic monitoring of a variety of conditions and disorders. They are also increasingly used by: patients themselves for at-home monitoring of such conditions and disorders; scientists for use in field testing for transgenic crops and environmental contaminates; soldiers in battlefield conditions for biological warfare weapon detection; and veterinary and emergency technicians for rapid testing, among others.

Included in the chromatographic techniques used in conjunction with immunoassays is a procedure known as immunochromatography. In general, this technique uses a labeling reagent or particle that has been linked to an antibody for the molecule to be assayed, forming a conjugate. This conjugate is then mixed with a specimen and, if the molecule to be assayed is present in the specimen, the labeling reagent-linked antibodies bind to the molecule to be assayed, thereby giving an indication that the molecule to be assayed is present. The labeling reagent or particle can be identifiable by color, magnetic properties, radioactivity, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. In the case of antigen detection, the sandwich immunochromatographic procedures call for mixing the sample that may contain the analyte to be assayed with antibodies to the analyte. These antibodies are mobile and typically are linked to a label or a reagent, such as dyed latex, a colloidal metal sol, or a radioisotope. This mixture is then applied to a chromatographic medium containing a band or capture zone. This band or capture zone contains immobilized antibodies for the analyte of interest. The chromatographic medium can also be in the form of a strip resembling a dipstick. When the complex of the molecule to be assayed and the labeled antibody reaches the zone of the immobilized antibodies on the chromatographic medium, binding occurs, and the bound-labeled antibodies are localized at the zone. This indicates the presence of the molecule to be assayed. This technique can be used to obtain qualitative results. Examples of sandwich immunoassays performed on test strips are described in U.S. Pat. No. 4,168,146 to Grubb et al., U.S. Pat. No.4,366,241 to Tom et al., U.S. Pat. Nos. 6,017,767 and 5,998,220 to Chandler; and U.S. Pat. No. 4,305,924 to Piasio et al.

In competitive or indirect immunoassays, the immobilized component is present in controlled amounts and the mobile component is present in unknown amounts. The unknown amount of mobile component is supplemented with a known amount of the same component that has been tagged by the addition of a measurable constituent which does not interfere with its immunochemical reactive properties. The tag may consist of a radioisotope, a chromophore, a particle, a fluorophor, or an enzyme. The amount of tagged material bound immuno-chemically to the solid phase will depend upon the amount of untagged component in solution competing for the same binding sites. The more of the unknown component present, the less will be the amount of bound tagged component.

Enzyme-based chromatographic assays are used in addition to immunochromatographic assays. These techniques are roughly analogous to immunochromatographic assays, but use an enzymatically-catalyzed reaction instead of an antigen-antibody reaction. The enzymatically-catalyzed reaction frequently generates a detectable product. Other analogous chromatographic assays are known. Although useful, currently available chromatographic techniques using test strips have a number of drawbacks. Many samples, such as fecal samples, contain particulate matter that can color the pores of the chromatographic medium, greatly hindering the detection of the labeling reagents. Other samples, such as blood, contain cells and colored components that make it difficult to read the test. Wet chromatographic medium is also difficult to read because of specular reflection from the chromatography medium.

Sample preparation and waste generation are responsible for other problems with currently available devices and techniques for immunochromatography. The increased prevalence of diseases spread by infected blood and blood fractions, such as AIDS and hepatitis, has exacerbated these problems. The available forms of lateral flow devices have a large portion of their components that are only used for mechanical support of the chromatographic membrane, and are not sealed, therefore making disposal a difficult, expensive and possibly hazardous procedure because of the presumed bio-hazards. Precautions have to be taken so that workers, or people who may inadvertently come into contact with the waste, do not become contaminated.

One common aspect of known devices, particularly in lateral flow technology, is that the assay is read visually, that is, by means of one or more optically readable lines on a test strip held in a carrier, which may have various configurations. There are several limitations or disadvantages to the known optically detected assays. Because they are optical, only surface changes (typically coloration) can be detected. The target analytes may be in the sample solution but of such a low concentration that only relatively few are captured in the capture zone in the porous membrane of the assay. This may provide a faint or even non-optically detectable line, and a false negative reading can result. Typically one end of the test strip is exposed to the sample, normally a fluid of some type, being tested for the particular target analytes of interest. The fluid migrates through the chromatographic medium whereby the analyte with its label is captured and immobilized, while the remaining fluid is absorbed into a medium at the distal end of the assay strip.

Examples of lateral flow assay methods and apparatuses, where the reading is normally conducted optically, are shown in U.S. Pat. Nos. 5,591,645; 5,798,273; 5,622,871; 5,602,040; 5,714,389; 5,879,951; 4,632,901; and 5,958,790.

Still another limitation on chromatographic devices currently available for use by the clinician or technician is their inability to perform quantitative assays. The labeled sandwich at the capture zone, or the decrease of label at the capture zone of a competitive assay, can only be read from the surface of the membrane, so only a relatively small portion of the label is read. Quantitative assessments are really only an estimation based on color intensity of the detection line. Because the prior art assays are optically read, they are subject to contamination by exposure and light-caused degradation. Optical assays also have a limited shelf life.

Another apparatus for detecting target molecules in a liquid phase is shown in U.S. Pat. No. 5,981,297 where magnetizable particles are employed and the output of magnetic field sensors indicates the presence and concentration of target molecules in the sample being tested. Other examples to sense magnetically using physical forces are disclosed in U.S. Pat. Nos. 5,445,970; 5,981,297; and 5,925,573. However, in these devices, the magnet requires relatively high power because the gap where the assay is placed must be wide enough to accommodate the relatively thick assay device.

SUMMARY OF THE INVENTION

Broadly speaking, the invention relates to lateral flow assay technology. In a preferred embodiment, it employs superparamagnetic particles as the labels for analytes to be detected. A device constructed according to the principles of the invention includes at least one analytical membrane and a housing that allow the detection or measurement of the label from the side of the membrane. In one embodiment, the bound complexes of labeled particles and analytes are captured in predetermined areas or regions on the test strip and the presence and quantity of labeled analytes are then readable by magnetic means. In additional embodiments, the detection of analyte may be accomplished by visual means, since the complexes also appear visually.

More specifically, in preferred embodiments, the invention is a lateral flow assay test device for quantitative detection of target analytes in a sample. In one embodiment, the device has a housing member shaped and configured to have two arms connected by a spanning portion, thereby generally forming a C-shape. The housing also has an interior space exposed on one side of the housing. A cover element is shaped and configured to enclose the interior space of the housing member. Positioned between the two arms is at least one analytical test strip. The strip is also sandwiched between the housing member and the cover. The strip is made up of a base member, an analytical membrane having a first end and a second end, a conjugate-containing element in contact with the first end of the analytical membrane, and at least one capture region in the analytical membrane somewhere between the first and second ends thereof, the capture region being configured to capture labeled analytes moving from the first end of the analytical membrane toward the second end of the analytical membrane. Additional embodiments have a sample receiving element at the first end of the analytical membrane. The C-shaped housing member allows, for example, a magnetic reader device for determining the presence and quantity of magnetic conjugate particle labeled target analytes, to read the test strip from the side, without removing the test strip from the housing.

A device according to several embodiments of the invention is constructed to allow the detector to access the test strip from the side of the test strip, rather than from the lengthwise axis. The test strip does not have to be removed from the cassette or housing in order to perform the detection step. The test strip can be read by an appropriate magnetic sensing device, and can be archived and reread at any time.

In one embodiment, the test strip in the invention preferably has a cover layer to create a sealed assay. The central portion of the test strip has a polyester film base layer, preferably Mylar®, and an adhesive layer on the base layer. A backed nitrocellulose layer is on top of the adhesive. On top of the nitrocellulose is another adhesive layer, and then a top cover layer.

The nitrocellulose layer preferably has at least two striped sections: a capture line and a magnetic index, or calibration line. They are preferably at right angles to the lengthwise axis of the strip. The stripes preferably permeate the nitrocellulose layer and are approximately 0.02" in width. In one embodiment, the calibration line is placed on the top cover layer, rather than on the nitrocellulose. In additional embodiments, there may be an additional procedural control line along with the capture and magnetic index lines. In a preferred embodiment, the minimum distance between any two adjacent lines is about 5 mm. This distance ensures that the detector reads only one line at a time. Therefore, it is contemplated that the distance between any two adjacent lines is determined by the limitation that the detector read only one line at a time.

In a preferred embodiment of the invention, the housing or cassette is generally C-shaped with the test strip spanning the two arms of the C-shape. The C-shape permits full access to the membrane or membranes to be measured by an appropriate measuring instrument, such as that described in U.S. Pat. No. 6,046,585. One advantage of the C-shape is to provide side access to the test strip, so the particular shape of the cassette or housing is not critical, only that the test strip be accessible from the side. However, in additional embodiments, the cassette may be constructed so as to contain more than one test strip. In these embodiments, the test strips may be parallel, may be disposed on different surfaces of the cassette, or a combination of both. For example, in one embodiment, the cassette may be generally square shaped, with one or more test strips on the exterior surface of each of the four sides. Other cassette shapes are contemplated herein, such as octagons, pentagons, and the like. It is therefore contemplated in the present invention that the shape and configuration of the cassette may be any that accommodates at least one test strip, while allowing detector access from the side.

The test strip also preferably has cavities at each end where the test strip is anchored or tensioned. These cavities enclose the sample and wick pads, respectively. The cavities may also have mounting posts at each end to align the test strip into the cassette. The ends of the test strip preferably have a portion of the adhesive on the polyester film that is exposed. This allows the strip to be held down around the posts. In addition, a sealant, such as silicone, may be placed onto the cassette frame, prior to strip placement, at the junction of the cassette and cover layer of the test strip. Final sealing of the cassette may be performed with a cover plate (having adhesive on one side) which seals and holds the back of the test strip in place over the cavities. A desiccant may be placed inside the web design or frame of the cassette, if desired.

In additional preferred embodiments, the completed cassette may have labels attached to the top surface. One label provides a means to seal the sample entry port. Another label contains test-specific information for both the human operator and the machine. The human-readable label contains the test type and expiration date. The machine-readable component has the calibration curve for the specific manufactured lot of reagents and the positions of the capture and magnetic index lines of the strip.

The physical arrangement of the present invention also allows for a thin laminate composed of the analytical membrane commonly used in the art, a bottom support and a top cover, to be measured in the magnetic field of the instrument and in close relationship to the detectors of such instrument. The test strip is preferably thin enough to fit within a reasonable sensor gap, while rugged enough to survive operator and machine handling. In a preferred embodiment, the test strip will be thin enough to fit within a core gap of about 0.5 mm. In addition, by being sealed and encased, the sample fluids and possible pathogens/analytes are prevented from contaminating the instrument, operator, and environment when being measured and disposed of. The test strip is also preferably pretensioned to allow it to pass through the detector without interference. It also allows the detector gap to be minimized, thereby improving sensitivity.

In alternate embodiments, the sample pad and conjugate pad housed in the cavity at one end of the cassette are assembled with variable pressure points to ensure reproducible contact to the various analytical membranes. The distal end of the cassette contains the wicking materials that act as the storage region for fluids after the assay has run. The cassette features the same mechanism of contact points as in the sample introduction end. In these embodiments, the characteristics of these pressure points may be varied. In a preferred embodiment, the pressure points are made from a flexible material, for example, silicone rubber.

Additional embodiments of the invention provide a removable cover to protect the analytical membrane during storage and transport prior to use. This cover does not actually make contact with the membrane, but instead is complementary to and fits into the C-shape of the housing.

The invention is also directed to a method for conducting a lateral flow immunoassay with quantitative detection of target analytes in a sample. The method involves applying the sample to one end of the porous membrane of a lateral flow test strip, coupling superparamagnetic conjugate particles residing in the test strip at one end, the superparamagnetic particles being treated to bind with any target analyte in the sample, capturing the bound complexes of analyte and superparamagnetic particles in the capture region of the porous membrane as the sample and bound complexes move through the porous membrane by capillary action, inserting at least a portion of the test strip sideways into a magnetic reader device, reading the quantity of labeled analytes in the capture region, and providing an output representative of the quantity of labeled analytes in the capture region.

BRIEF DESCRIPTION OF THE DRAWING

The objects, features and advantages of the invention will be more clearly perceived from the following detailed description when read in conjunction with the accompanying drawing, wherein.

DETAILED DESCRIPTION OF THE PREFERRED EMBODIMENTS

A particular advantage of the invention is the greatly improved sensitivity of the device over known lateral flow techniques. It also provides a very rapid measurement of the analytical region in the test strip. In addition, by providing the detector with access to the test strip from the side of the strip, rather than from the end of the strip, the gap between the detector elements can be relatively small. This is because the space between the detector elements does not have to be large enough to accommodate the relatively thick sample pad or wicking pad, which otherwise would be the case if the test strip were inserted into the detector lengthwise. Consequently, in the present invention, the electromagnet requires less power than does an end loading detector.

There are also many advantages of using magnetic particles over known colored particles or other optical indicators in the prior art. Linearity is an advantage because magnetic detection is linear with respect to the amount of magnetic material present over a wide range, through at least four orders of magnitude. Time stability is also significant because magnetic particles are stable. The developed assay is available to be archived and retested as necessary. Further, magnetic particles are generally inert to biological systems and the environment so they not only remain stable, but they are environmentally and biologically safe. Further, magnetic particles are already in widespread use throughout the diagnostics industry with other technologies so they are readily available.

Other benefits of magnetic detection are that since the particles are superparamagnetic, they are magnetic only when in a magnetic field. This allows them to be freely manipulated in solution without aggregating. It is also contemplated herein that detection of analytes may be accomplished by visual means. Magnetic conjugate particle labeled target analytes may also provide a visual indication on the test strip. This is a qualitative indication. If a quantitative indication is desired, the magnetic reader device is employed.

Another significant advantage over the prior art optical lateral flow devices is that with this invention the total amount of analytes in the capture region of the test strip is measured as a single mass in one volumetric measurement by magnetic means. The permeability of magnetic fields is such that any magnetic label contained within the active region of the detector will be detected. This contrasts with optical sensing techniques in which only reporter-analyte interactions on or very near the surface are detectable. In this invention the strength of the magnetic signal increases directly with the mass of magnetically detectable material, typically magnetite ($Fe_3O_4$), involved. This inherent linearity of magnetic detection contributes to sensitivity, accuracy and dynamic range. Finally, superparamagnetic particles are physically similar to colloidal gold in size, and may be easily adapted to a wide range of lateral flow assays. It is noted that colloidal gold, as well as fluorescent latex particles, are typically employed in the prior art optically sensed immunological assay techniques.

In lateral flow technology, at one end of the porous membrane (the active part of the test strip) is the sample introduction area conventionally comprising a sample pad and a conjugate pad. In prior devices, the conjugate pad was the source of freely moveable colored particles, typically gold sots from colloidal gold, or fluorescent latex particles. In the present invention, the moveable particles are the superparamagnetic particles, which label the target analytes from the sample being introduced through the sample pad. The sample, together with the bound magnetic particle labels and target analytes, move with capillary action along the porous membrane and are captured in a predefined location called a capture region or capture zone. There may be more than one capture zone to enable multiplexing, which is testing for more than one type of analyte at the same time in the same test strip. Excess analytes and the carrying liquid continue to move on through the capture zone to the opposite end of the porous membrane, sometimes forming a control line or zone separate from the capture zone. If a signal is detected in the control zone, the operator is assured that the analyte has passed the capture zone and that the test is functioning.

Typically a wicking pad is mounted on the far end of the porous membrane to receive excess fluid. Capillary action drives the flow from the introduction at one end of the porous membrane through the entire length of the membrane. In the present invention the wicking pad is in contact with one end of the chromatographic membrane.

Several embodiments of the present invention have a test strip employing superparamagnetic particles as the labels for the analytes to be detected, where, as an additional feature, the analytical strip is housed in a cassette that is constructed so as to allow the detector to access the test strip from the side, rather than from the lengthwise axis of the test strip. The test strip is also preferably sealed and disposable along with the cassette. The only limitation on the shape or geometry of the cassette is that it should be constructed to allow the detector to access the test strip from the side, rather than from the lengthwise axis of the test strip. In a preferred embodiment, as shown in the accompanying drawing, the cassette is generally C-shaped with one or more test strips spanning the two ends of the C-shape. However, any shape or configuration is contemplated herein so long as side access is maintained.

The benefits of the C-shaped embodiment, aside from the improved access to the analytical membrane, relate to the convenience and simplicity of the sample introduction area, the variability of the volumes of sample introduction, and the means to wick or take up all of the sample volume after performance of the assay. These features are accomplished by the arms or ends of the cassette, which contain the conventional materials of lateral flow technology. The sample introduction is also sealed after application of the sample by an adhesive coated membrane.

Figure 1A:
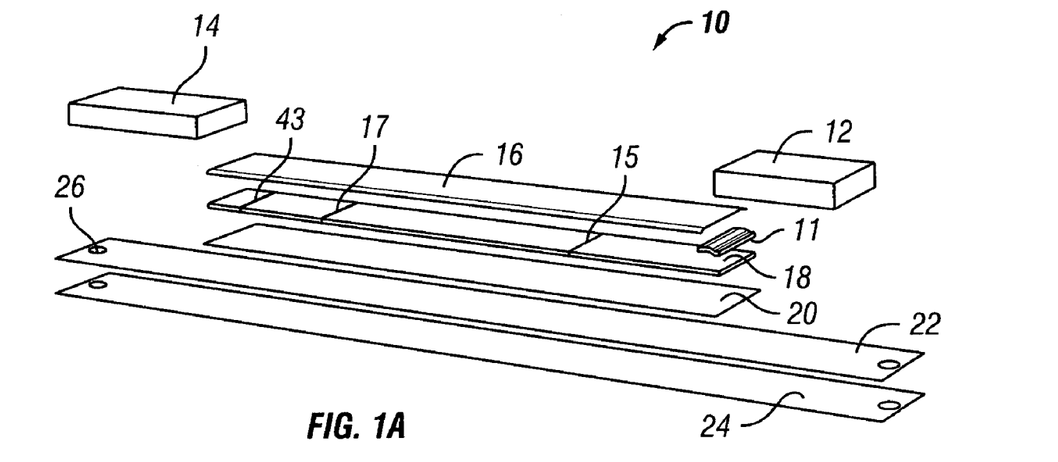
FIG. 1A shows an exploded view of the components of an embodiment of a test strip formed in accordance with the invention.

With reference now to the drawings, and more particularly to FIG. 1A, there is shown an exploded view of an embodiment of the test strip of the present invention. Test strip 10 has base member 24, adhesive 22, backing member 20, porous membrane 18, and cover layer 16. In a preferred embodiment, the base member is a polyester film, such as Mylar®, and the porous membrane is a nitrocellulose. Conjugate pad 11 and sample pad 12 are in contact with one end of the strip. The conjugate and sample pads act as the source and method of distribution of the sample to the porous membrane. Wick pad 14 is shown in relation to the other end of the strip.

Within the conjugate pad, or at the beginning of the porous membrane, as in another embodiment where the conjugate pad is not present, are superparamagnetic beads or particles which are coupled to antibodies. The combination of a particle or bead, and an antibody is referred to as a conjugate, a plurality of them being the label of the analyte. These conjugates are configured to combine with the target analytes in the sample solution in a known manner to create a sandwich assay, well known in the art, within the analytical capture zone 15 and the control capture zone 17. Holes 26 are on either end of the strip and provide means for locating the strip in the cassette.

Figure 1B:
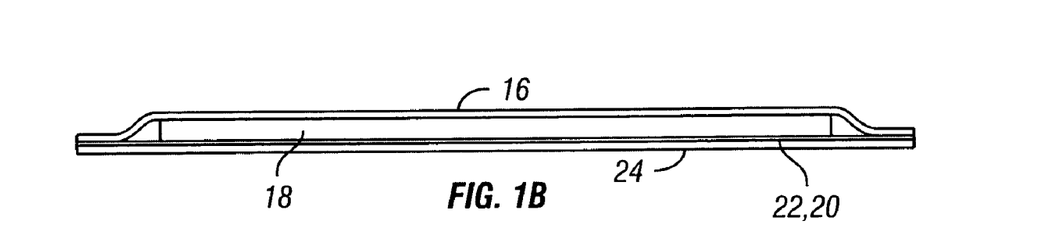
FIG. 1B shows an assembled longitudinal cross-sectional view of the components of the test strip of FIG. 1A.

FIG. 1B shows the central portion of the test strip in an assembled view. Base member 24 has adhesive 22 and backing member 20 on top of it. Above that is positioned porous membrane 18, which is covered by cover layer 16.

Although a sandwich assay has been described above, it is also contemplated herein that competitive assay techniques could be employed. The capture zone is formed by striping with antigens or antibodies, for example, as is well known. The fluid of the sample travels from right to left in FIGS. 1A and 1B within the analytical membrane because of the capillary action, first by porous membrane 18 and then by wick pad 14. The wicking pad enhances capillary flow by "pulling" or "driving" the fluid and allows for the total sample to be absorbed by the wick. This volume of liquid required for the assay is known as the total bed volume of the analytical membrane.

Cover layer 16 of the assay device may be, for example, plastic, glass, paper, or any practical combination thereof. Printed standard or calibration line 43 may be situated on cover layer 16 and provide information utilized by the assay reader after the test has been accomplished. These lines are contemplated to be magnetic or optically reflective, or a combination thereof. These standard or calibration lines contain information that the assay reader needs, for example calibration curves, test identification and analytical procedures.

The wick in contact with the end of the analytical region of the porous membrane stores the excess liquid of the sample. Conventional wick materials contain the bed volume of the membrane within the assay device. This containment of the sample in a sealed device allows the entire device to be disposable and non-contaminating, an aspect not typically found in other assay devices.

At the right end, as shown in FIG. 1, is sample pad 12, through which an analyte-containing sample solution is administered to the porous membrane. The sample pad may also include conjugate pad 11 in communication with the porous membrane.

While the capillary action and the existence of a capture zone and control zone are well known and conventional, the manner in which the described embodiments of the invention detect the presence and the quantity of the target analytes differs greatly from prior devices. The analytical membrane is contained in a thin and sealed laminate and, as well, the fluid of the sample is directed to flow through the porous membrane to the wick. A significant feature of this embodiment is that the magnetic detecting device does not measure non-specifically bound magnetic labels or particles, since they have passed by the capture/control zones to a place outside of the read area of the magnetic sensing device. In one embodiment, the read area of the device is about 2 mm in width. The capacity of the wicking pad is known so that the bed volume capacity is well absorbed and that the analytical strip is the only component of the assay that the magnetic sensing device measures.

As previously stated, prior art lateral flow assays depend upon color or fluorescence to provide a visual or optical indication of the presence of target analytes in the capture zone, and the ability of optical techniques to detect the presence of the target analytes is limited. A relatively low concentration of target analytes in the sample can result in so few captured analytes as to be optically undetectable on the surface of the porous membrane at the capture zone. Further, the optical intensity of the capture zone with the captured analytes is only a rough function of the quantity of target analytes captured. However, there is no way to accurately measure the total quantity of captured analytes within the capture zone because only the surface is optically readable. The present embodiment provides greatly enhanced sensitivity and quantitative accuracy because the magnetic labeled analytes in the capture zone are detectable by a suitable magnetic detector to the extent of the target analytes within the entire volume of the capture zone.

Additional features may be added, including additional capture zones (two are shown in all figures) and additional calibration lines. There could be several capture zones and equivalent calibration lines.

Figure 2:
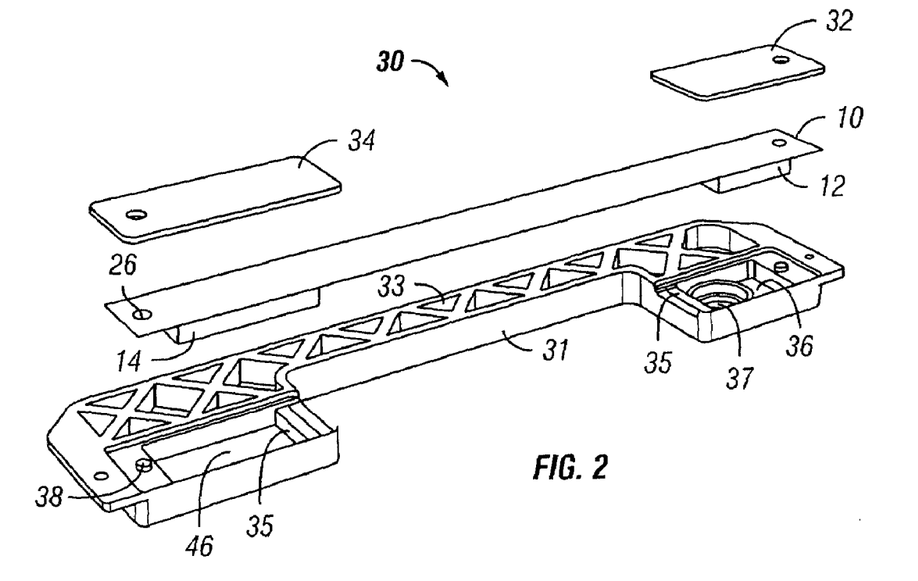
FIG. 2 is an exploded bottom view of a test strip and a cassette in accordance with an embodiment of the invention.
Figure 3:
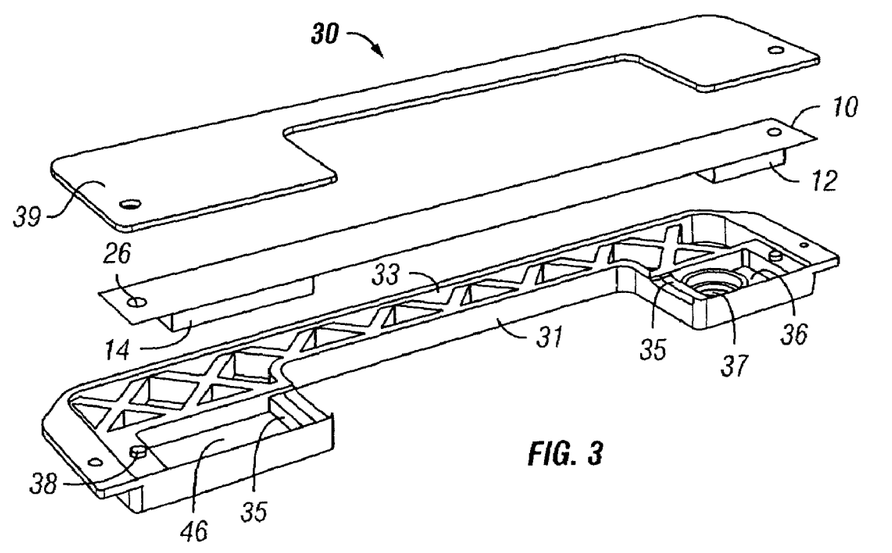
FIG. 3 is an exploded bottom view of an alternate embodiment of the invention with a single cover layer.

Referring now to FIG. 2, generally C-shaped cassette 30 is shown in an exploded bottom view. Test strip 10 is placed across the open space between the ends of the cassette, with sample and wick pads 12 and 14, respectively fitting into cavities 36 and 46. Alignment hole 26 engages post 38 to ensure proper alignment. Adjustable pressure pads 35, which are located just inside the cavities on the arms of the cassette, provide a specific amount of pressure to the test strip so that it performs as desired. When cover layers 32 and 34 are placed over the ends of the test strip to ensure that the device is sealed, a pressure on the test strip is formed. The amount of pressure is one factor affecting the rate of fluid flow through the strip. In the embodiment shown in FIG. 3, cover layers 32 and 34 are combined into a single cover layer 39, which also covers practically the entire bottom surface of the cassette. In this embodiment, a desiccant (not shown) may be placed within the web design, under cover layer 39, thereby improving the storability of the assay device.

Also as shown in FIGS. 2-5, cavity 36 has sample port 37 disposed therein. The sample port is constructed so that it comes into contact with sample pad 12 when assembled. The sample port has a funnel structure extending downward within the cavity and contacting the sample pad. This contact ensures that when sample material is added, the sample pad does not become flooded. Instead, the sample is absorbed by the sample pad more consistently, thereby further contributing to a uniform fluid front on the strip.

The cassette may be formed of any suitable rigid material, such as plastic or the like. In a preferred embodiment, as shown in FIG. 2, additional strength to the cassette is provided by web design 33. Other structural shapes may be employed. In addition, although the C-shaped expanse is shown, indicated by reference numeral 31, it is contemplated herein that any other shape is within the scope of the invention, as long as that shape allows the detector to access the test strip without having to pass over the cassette, the sample pad, or the wick pad.

Figure 4:
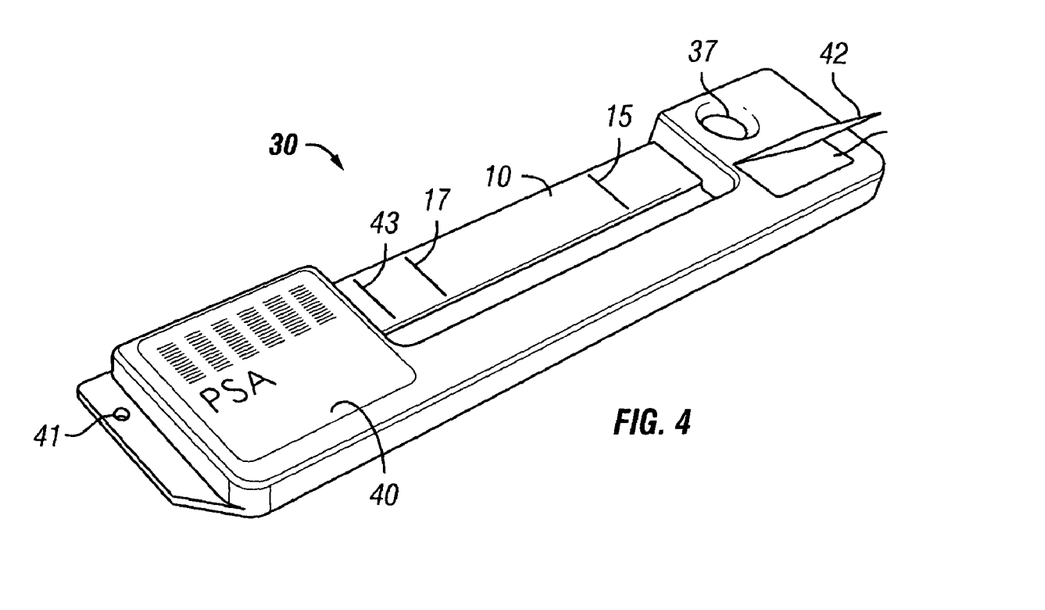
FIG. 4 shows an assembled view of the FIG. 2 or 3 test cassette.

At the right end, as shown in FIG. 4, is sample port 37 through which the analyte-containing sample solution is administered to the porous membrane via the sample and conjugate pads. Label 40 contains both human and detector readable information. It may contain calibration information for the detector, as well as test and date information for the user. Sample port 37 may be sealed by folding over sealing flap 42. Alignment hole 41 is configured to engage with the transport mechanism of the magnetic reader, which is described below, and shown in FIG. 6.

Figure 5:
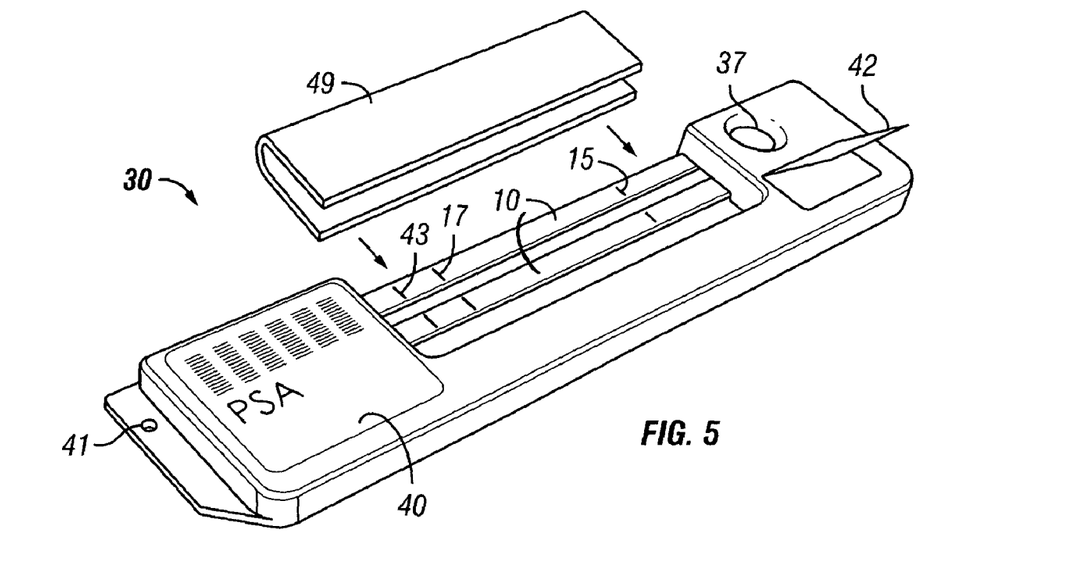
FIG. 5 shows an assembled view of an alternate embodiment of the invention with multiple test strips therein and a protective cover.

Referring now to FIG. 5, another embodiment of the invention in which more than one test strip is located in the cassette is shown. In this embodiment, two test strips 10 span the C-opening in parallel. In addition, cover 49 is shown as fitting over the C-opening, thereby protecting the test strips.

Figure 6:
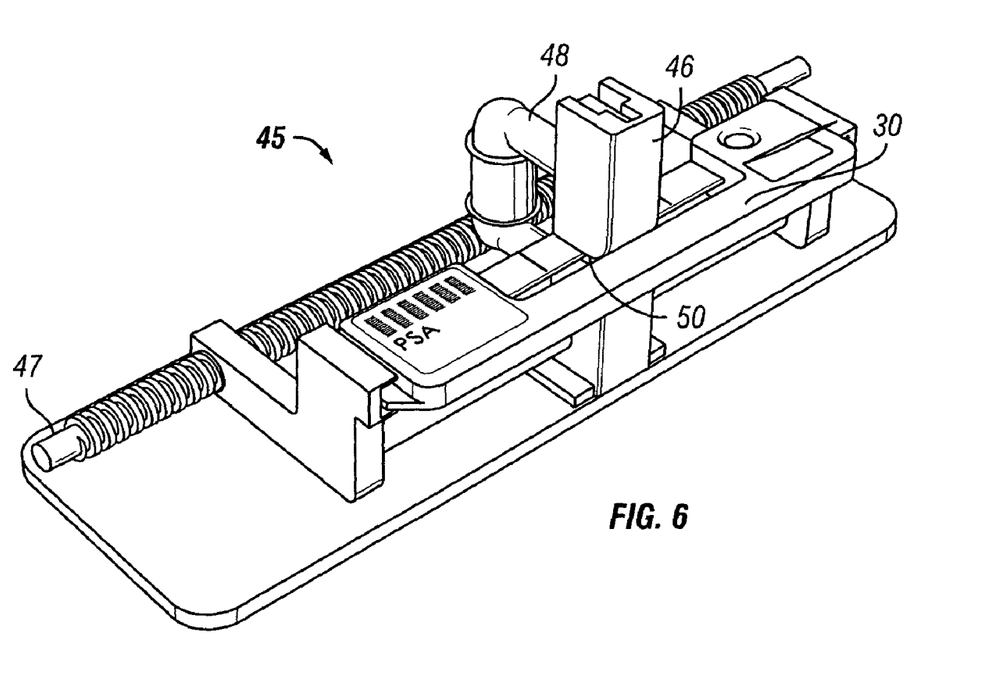
FIG. 6 shows how the test strip of an embodiment of the invention may be positioned in a magnetic reader device.

A significant aspect of an embodiment of the invention is the means and manner of magnetically reading the assay. A magnetic reader of the type contemplated is shown in FIG. 6. This employs the technology disclosed in PCT publication WO 99/27369, to determine the presence of target analytes and their quantity. As shown in FIG. 6, reader 45 (external cover not shown) is preferably portable, that is, approximately pocket size, so that it is easily employed in the field. Other embodiments can have larger footprints, for use in a laboratory. The pocket size device will provide accurate assay readings even under stressful conditions and in poor light. The apparatus of FIG. 6 has "C" shaped coil 48, gap 50 between reader heads 46 and transport mechanism 47, which is shown as a screw drive. However, other suitable transport mechanisms known to those skilled in the art are also contemplated herein. The accurate analyte quantity may be shown in a display window, which could be an LED or an LCD screen, for example (not shown).

In the embodiments disclosed herein, the test strip is placed within gap 50. Accordingly, sensor coils are positioned on both sides of the test strip when the test strip is introduced. One advantage of this arrangement is that the magnetic measurement is less sensitive to the vertical position of the test strip within the gap in the coil.

The test strip is preferably made thin so that the reader of FIG. 6 can read the analytes in the capture zones. It is also preferably firmly secured and relatively rigid, with the bed volume of the assay and any excess fluid encased within the sealed wick member of the disposable assay device. As shown in FIG. 6, detector 46 is able to access the test strip from the side of the strip, rather than from the lengthwise axis of the test strip. Accordingly, magnet 48 does not require a relatively large gap to accommodate the sample and or wick pads, because those pads do not pass through the detector.

It is contemplated that the test strip, primarily consisting of the porous membrane, hydrophobic barrier and top and bottom covers or laminates, be made sufficiently rigid to need a minimum support from the ends of the cassette. Such a configuration would make the assay device easy to handle and to archive. FIG. 1A shows how the test cassette, comprised of the cover, porous membrane, hydrophobic barrier and bottom cover or membrane, is assembled. This completed test region can be typically about 2 to about 15 mm wide, and only about 150 to about 500 µm thick. This strip is easily fed into reader for a digital readout, which may be shown on the screen or printed on paper in any desired form by the user. Transport 47 moves cassette 30 thereby positioning desired portions of the strip under reader 46. The exposed analytical membrane is stable and can be archived either before or after being read. Since the superparamagnetic beads are magnetized only during the reading process, the exposed test strip is not subject to degradation. The analytes contained in the capture zone remain there, labeled with the conjugate combination.

Contrary to prior art optical lateral flow assays, where very faint lines can easily be misinterpreted in the field, especially in stressful situations or low light conditions, there is no possibility of misinterpretation of test results with this invention. Optically read assays, especially those visually read, are also subject to operator error or bias, or both. In the present invention the reader accurately measures the total number of labeled analytes in the capture zone without inherent sources of error as mentioned above.

Since the test strip may actually touch the detector, as shown in FIG. 4, without the protective cover surface the porous nitrocellulose membrane could be damaged by rubbing across the detector, thereby possibly producing incorrect or unreliable readings, or both. Although being very thin, in the range of about 0.025 mm to about 0.1 mm, the cover protects against physical damage and environmental contamination as well as providing precise positioning for accurate electromagnetic readings.

The invention has been illustrated and described by means of specific embodiments. It is to be understood that numerous changes and modifications maybe made therein without departing from the scope of the invention.

What is claimed is:

1. A lateral flow assay test device for detection of target analytes in a sample, said device comprising:
    a housing member shaped and configured to have two arms connected by a spanning portion, thereby generally forming an open space between the two arms, the housing also having an interior space exposed on one side of the housing;
    a cover element shaped and configured to enclose the interior space of the housing member;
    at least one analytical test strip having first and second ends and being positioned between the two arms, the strip also being at least partially sandwiched between the housing member and the cover element, the strip comprising:
        a base member;
        an analytical membrane having a first end and a second end;
        a conjugate pad at the first end of the analytical membrane; and
        at least one capture region in the analytical membrane intermediate said first and second ends thereof, said capture region being configured to capture labeled analytes moving from said first end of said analytical membrane toward said second end of said analytical membrane;
    the open space in the housing member being shaped and configured to provide lateral access to the test strip and to enable the determination of the presence of target analytes in the capture region of the test strip while the test strip remains mounted to the housing.

2. The device of claim 1, further comprising a sample receiving element at the first end of The analytical membrane.

3. The device of claim 1, wherein The open space in the housing member is shaped and configured to provide lateral access to the test strip to enable a magnetic reader device to determine The presence and quantity of magnetic conjugate particle labeled analytes in the capture region of the test strip while The test strip remains mounted to the housing.

4. The device of claim 3, and further comprising a protective membrane covering said analytical membrane and a backing member on the side opposite to said protective membrane, said protective membrane also being optically non-transparent.

5. The device of claim 4, wherein said protective membrane is formed integrally with said analytical membrane.

6. The device of claim 4, and further comprising at least one magnetic calibration line printed on said protective membrane.

7. The device of claim 4, wherein said protective membrane is formed of material selected from the group consisting of plastic, glass and paper.

8. The device of claim 3, wherein said conjugate is disposed in a conjugate containing element that is in fluid flow contact with the first end of the analytical membrane.

9. The device of claim 3, wherein said conjugate further comprises superparamagnetic conjugate particles, said particles being configured to bind with target analytes in the sample.

10. The device of claim 1, and further comprising at least one control region in the analytical membrane intermediate said first and second ends thereof, said at least one control region being configured to collect conjugates that have passed the capture region to show that the test strip has been used.

11. The device of claim 1, and further comprising a wicking element at the second end of the analytical membrane.

12. The device of claim 1, wherein multiple analytical test strips are placed parallel between the two arms of the housing.

13. A lateral flow assay test device for detection of target analytes in a sample, said device comprising:
    a housing member formed with two spaced arms defining an open space therebetween, the open space being externally accessible, the housing member having an interior space exposed on one side;
    a cover element shaped and configured to enclose the interior space of the housing member; and
    at least one elongated analytical test strip having first and second ends and being mounted to the housing, the ends of the test strip being partially sandwiched between the housing member and the cover at the two spaced arms thereby spanning the open space, the strip comprising:
a base member;
an analytical membrane having a first end and a second end;
a conjugate containing element in contact with the first end of the analytical membrane; and
at least one capture region in the analytical membrane intermediate said first and second ends thereof, said capture region being configured to capture conjugates moving from said first end of said analytical membrane toward said second end of said analytical membrane;
the open space in the housing member being shaped and configured to provide external access to the test strip from above, from below, and from the open space side to enable the determination of the presence of target analytes in the capture region of the test strip while the test strip remains mounted to the housing.

14. The device of claim 13, further comprising a sample receiving element at the first end of the analytical membrane.

15. The device of claim 14, and further comprising a wicking element at the second end of the analytical membrane, wherein the housing has cavities shaped and configured to accommodate the sample receiving element and the wicking element.

16. The device of claim 13, wherein the open space in the housing member is shaped and configured to provide lateral access to the test strip to enable a magnetic reader device to determine the presence and quantity of magnetic conjugate particle labeled analytes in the capture region of the test strip while the test strip remains mounted to the housing.

17. The device of claim 16, and further comprising a protective membrane covering said analytical membrane, and a backing member on the side opposite to said protective membrane, said protective membrane also being optically non-transparent.

18. The device of claim 17, and further comprising variable pressure pads located at the junction of the housing and the protective membrane on opposite sides of the open space.

19. The device of claim 18, and further comprising a sealant disposed on the housing at the junction of the housing and the protective membrane.

20. The device of claim 13, wherein the housing is square shaped and a test strip is positioned on at least one side thereof.

21. The device of claim 13, and further comprising a wicking element at the second end of the analytical membrane.

22. The device of claim 13, and further comprising a desiccant placed within the interior space of the housing.

23. The device of claim 13, and further comprising a label on the top surface of the housing.

24. The device of claim 16, wherein the test strip is thin enough to fit within about a 0.5 mm gap in the magnetic reader device.

25. The device of claim 13, wherein the test strip is tensioned along its lengthwise axis.

26. The device of claim 13, and further comprising a rigid removable cover placed over the at least one test strip that protects the test strip during storage and transport.

* * * * *